(12) United States Patent
Kean et al.

(10) Patent No.: US 6,611,133 B2
(45) Date of Patent: Aug. 26, 2003

(54) ANODE ROD DEPLETION INDICATOR

(75) Inventors: James G. Kean, Madison, NJ (US); Matthew Cugliari, Nutley, NJ (US)

(73) Assignee: Atlantic Professional Services Inc., Clifton, NJ (US)

( * ) Notice: Subject to any disclaimer, the term of this patent is extended or adjusted under 35 U.S.C. 154(b) by 0 days.

(21) Appl. No.: 09/793,281

(22) Filed: Feb. 26, 2001

(65) Prior Publication Data

US 2001/0045820 A1 Nov. 29, 2001

Related U.S. Application Data

(60) Provisional application No. 60/185,511, filed on Feb. 28, 2000.

(51) Int. Cl.[7] .............................................. G01N 27/00
(52) U.S. Cl. ...................................................... 324/71.1
(58) Field of Search ............................... 324/71.1, 71.2, 324/699, 700; 73/40.7, 61.61, 86; 204/404; 422/53; 116/200, 206, 227; 205/730, 733, 775.5; 340/815.4

(56) References Cited

U.S. PATENT DOCUMENTS

| | | | |
|---|---|---|---|
| 3,037,920 A | 6/1962 | Vixler | 204/148 |
| 3,621,810 A | 11/1971 | Zuck, Jr. | 116/114.5 |
| 3,978,309 A * | 8/1976 | Strobach | 219/104 |
| 4,017,714 A * | 4/1977 | Kreiser | 219/322 |
| 4,051,007 A * | 9/1977 | Hossle | 204/197 |
| 4,090,170 A | 5/1978 | Lincklaen-Arriens et al. | 340/5 R |
| 4,271,120 A | 6/1981 | Michaud | 422/53 |
| 4,514,730 A | 4/1985 | Ming | 340/815.26 |
| 5,243,298 A | 9/1993 | Runner | 324/700 |
| 5,253,674 A | 10/1993 | Argyle et al. | 137/559 |
| 5,373,728 A | 12/1994 | Guentzler | 73/40.7 |
| 5,948,971 A | 9/1999 | Brooker et al. | 73/86 |

* cited by examiner

Primary Examiner—Christine Oda
Assistant Examiner—Etienne P. LeRoux
(74) Attorney, Agent, or Firm—Klauber & Jackson

(57) ABSTRACT

An Anode Rod Depletion Indicator for use with a sacrificial anode in a fluid storage tank. A core wire, which is arranged within the anode, has a series of hollow or fluted passageways. When the anode depletion causes a predetermined amount of the core wire to be exposed, fluid contained in the storage tank flows in the hollows or flutes of the core wire. The fluid pressurizes and activates a pressure gauge or switch, or pushes a piston up to a location, which is visible to the owner. In an embodiment, a visible indicator such as "Good" is visible on a pressure gauge until the fluid pressure indicates "Replace" on the pressure gauge or until the piston pushes up a "Replace" indicator to the need to replace anode rod, to prevent corrosion and failure of the tank, while the anode is still providing corrosion protection of the tank. An electrical switch may cut off supply fluid, fuel supply, and/or activate an alarm.

20 Claims, 7 Drawing Sheets

ANODE ROD DEPLETION INDICATOR

This application claims the benefit of U.S. Provisional Application No. 60/185,511, filed Feb. 28, 2000.

BACKGROUND OF THE INVENTION

1. Field of the Invention.

The present invention relates to anode rods used to prevent corrosion of a metal tank. More particularly, the present invention relates to a depletion indicator for anode rods contained in the tank of a pressure vessel, such as a water heater or boiler.

2. Description of the Related Art.

It is known in the art that an average residential water heater should last approximately 10 to 12 years. Almost all of the components of a water heater can be repaired or replaced except for the tank. Once the tank rusts through and leaks water, there is no way to repair the water heater. Replacement is the only solution.

A water heater has an internal sacrificial anode rod to protect the tank from rusting. An anode's sole purpose is to corrode so that the steel of the tank does not corrode, i.e., rust.

The following is an incorporation of a detailed explanation of anode rods and cathodic protection in residential water heaters as provided in Technical Service Bulletin #1201, updated Sep. 24, 1998, issued by the Rheem-Ruud Manufacturing Company:

"Corrosion can be defined as the destructive attack of a metal by an electrochemical reaction with its environment. Steel exposed to moisture and oxygen will rust and corrode. Corrosion is defined as the "eating away" of metal by electrochemical means. There are four main factors affecting water's ability to corrode:

1. Acidity

Water is made acidic by naturally occurring dissolved gases such as carbon dioxide.

2. Temperature

Higher temperatures speed up the corrosive process.

3. Electrical Conductivity

The more dissolved mineral solids in the water, the greater its ability to carry electrical current. When dissimilar metals are in the water, electrical current flows between the metals. One of the metals gradually corrodes faster than the other.

4. Amount of dissolved oxygen

Free oxygen dissolved in the water promotes corrosion.

Dissimilar metals are present in the interior steel tanks surfaces of all water heaters in several forms such as the drain nipples, heating elements, immersion thermostats, inlet and outlet nipples. These metals, and others present in the water itself, combined with the oxygen content of the water and heat, establish an environment conductive to corrosion. The dissimilar metals create a corrosion cell that is enhanced by the conductivity of the water. The anode is put in to overcome (neutralize) the corrosive cell.

In a water heater, corrosion is protected by a glass (actually a porcelain enamel) lining in the steel tank, and the use of auxiliary anode rods. During the manufacturing process, the inside water tank and both the top and bottom heads are sprayed with a slurry of glass material. This material is fired in a furnace, and when cooled, resembles a glass coating called porcelain. This glass provides a long life to the steel tank; otherwise the tank would fail or corrode in a relatively short time. Every glass-lined water tank, no matter how carefully it is manufactured, has some bare metal exposed. This is due to the inability to effectively cover sharp corners and the radius around the fittings. There is a chance that a crack or chip in the porcelain lining will allow the water to come in contact with the steel tank. Over time, water, a universal solvent that becomes more aggressive with temperature, slowly dissolves the interior tank lining. Thus, the exposed bare metal will create conditions for corrosion, starting as pin holes in the tank and finally tank failure.

Cathodic protection is accomplished in the glass-lined water heater through the use of an auxiliary magnesium anode. Due to the relative position of magnesium to steel in the electromotive series of metals, magnesium will corrode, producing an abundance of electrons which flow (much the same as electrical current) to the exposed steel surface and maintaining it in the electro-negative state. As current flow takes place, the anode rod reacts chemically to corrode at a rate faster than the steel inner tank. This process stops tank corrosion by substituting the sacrificial magnesium anode rod in place of the steel tank. As long as the magnesium anode rod remains in the tank, in an active state, there will be no corrosion of the minute areas of exposed steel inside the tank.

The life of the anode, in turn, depends on water temperature, amount of water used, and the quality of the glass lining. However, the most important factor in the life of the anode rod is the water chemistry, the hardness or softness of the water. Also check the manufacture and installation date of the water heater. If the heater is more than five (5) years old, and the anode rod has not been replaced, inspect the anode rod. The anode should be replaced when there is six (6) inches or more exposed core wire at either end."

Additionally, in Rheem-Rudd's Technical Service Bulletin #1401, "Standing Pilot Gas Water Heater Maintenance," updated Sep. 24, 1998, Section 2, "Anode Rod Inspection," it states that:

"The anode rod should be removed from the water heater's tank annually for inspection and replaced when more than 6" of core wire is exposed at either end of the rod. Refer to your Use and Care Manual for anode rod location. Make certain [the] cold water supply is turned off before removing anode rod."

Virtually all water heater manufacturer's inspection and maintenance instructions recommend that the anode rod be removed from the hot water heater tank annually for inspection by the homeowner or a technician, as the case may be. Since many consumers have little knowledge of this recommendation and therefore fail to inspect the condition of the anode rod, or fail to have a trained technician inspect the condition of the anode rod, there has been a long felt need for a way to determine when the anode rod requires replacement without any complicated and costly inspection procedures.

Moreover, a recently published (January 2001) brochure from PSE&G, New Jersey's electric and gas company, advises customers to be aware of the telltale signs of failing water heaters, including, among other things, that water is leaking from the tank, that the hot water is discolored or rusty, or that the water heater is over ten years old.

It is clear from PSE&G's brochure advising customers of these signs of water heater failure and suggesting that customers replace their tanks based solely on the age of the tank, that customers are not periodically inspecting/replacing the anode rod as recommended by the manufacturer.

Homeowners, however, should not rely upon these occurrences to detect a problem with the water heater. Indeed, once water is leaking from the tank and/or hot water is discolored, enormous and costly damage may have occurred or will occur shortly.

Thus, there has been a long-felt need in the industry for a way to preserve the structural integrity of the fluid tank in a pro-active manner, rather than in a reactive manner (from age, rusty water or leaks), to replace the often-neglected annual inspection of the anode and to save the consumer the enormous costs that can be associated with water heater failure.

The present inventors under took an assessment of the recommended inspection procedures to determine whether the common-place neglect of the annual inspection could be due to the difficulty of complying with the procedures.

The results showed that the requirements and procedures of annually inspecting the anode rod are unrealistic, overly complex, and difficult for the typical homeowner in the following ways:

The removal of an anode rod for inspection is a highly technical task requiring competence, physical dexterity, expertise, skill, and tools. The primary problem is the lack of headroom in almost all installations. For example, the length of a Rheem-Rudd replacement anode rod is approximately 44 inches, but it could be any length or diameter according to need. The hot water heater must be tilted if there is insufficient headroom for a direct removal and replacement of the anode rod. This is a common occurrence considering that a water heater may be 6 feet high or more, and have pipes connected to its top. Thus the clearance necessary to remove a long anode rod is substantial. Tilting the water heater is a major task that should not be performed solely by the homeowner. The job requires removal of 4 connections:

(1) The inlet cold water line,
(2) the outlet hot water line,
(3) the inlet gas or oil connection line, and
(4) the flue draft hood and vent pipe.

In addition, the tank should be drained since it may contain hot water that could scald the homeowner. Tilting the tank requires at least two persons for safety.

After the tank is tilted, the anode rod can be removed and examined. If the rod requires replacement, the new rod is inserted and tightened. The above procedure is then repeated in reverse order to reinstall the hot water heater.

This procedure requires the homeowner to purchase a spare anode rod just in case the old anode rode requires replacement, or the water heater must remain disassembled until the homeowner returns from the appropriate supplier with a replacement. If a replacement rod must be ordered, the homeowner must reconnect the old rod and go through the entire process again to install the new anode rod after receipt of same.

It is unreasonable to require the homeowner to undergo the expense of having a replacement anode rod in his or her home for a possible future replacement requirement. If the manufacturer deems it necessary, it should supply a replacement anode rod with each hot water heater. If the anode rod is intact and no replacement is necessary, all of this is unnecessary.

As an experiment, the present inventors visited several plumbing supply and home improvement stores to purchase replacement anode rods, and were informed that they do not stock such items. It was necessary to contact the manufacturer directly to obtain a replacement anode rod. It took several days from the date of ordering until the present inventors received the replacement anode rod.

In addition, several plumbing contractors were contacted to determine if they could inspect the anode rod on a water heater. The plumbing contractors recommended that the anode rod first be ordered from the manufacturer and obtained prior to the inspection, in the event it was necessary to replace the anode rod. Otherwise, if the rod is not replaced at the time of inspection, the cost would increase significantly because two trips would be required by the contractors.

The contractors cost to perform this work would be approximately 2 hours at $50.00 per hour=$100.00. The cost for the replacement anode rod would be an additional $20.00–$30.00. The potential annual maintenance cost of the water heater related only to the anode rod, therefore, is approximately $100.00–$130.00.

Some manufacturers of water heaters state that the anode rod should be inspected annually and replaced when more than 6" of core wire is exposed at either end of the rod. Supposing that an annual inspection of the anode rod determined that there is only 4"–5" of exposed core wire at either end, according to the manufacturer, the rod does not require replacement. The homeowner/consumer would reasonably assume that the rod would still function satisfactorily protecting the tank for the entire next year.

However, the homeowner/consumer may fail to adequately estimate the amount of hot water usage over the next year and on the next annual inspection of the rod there could be 8"–10" of exposed wire core at either end. This extreme condition of core wire exposure poses a much more serious problem. Due to the excessive depletion of the anode rod beyond six inches, it is likely that the integrity of the steel water heater tank has been compromised due to corrosion resulting from the lack of adequate protection from the anode rod.

For these reasons, the present inventors have determined that the manufacturer's recommendations are not reasonable, and that a reasonable alternative design of the anode rod must be accomplished.

The alternative design of the anode rod developed by the present inventors provides the maximum protection of the tank possible and satisfies the demonstrated long felt need in the industry with a device which eliminates the required annual maintenance costs incurred by the homeowner to unnecessarily remove and inspect the anode rod.

There have been some attempts in the prior art to overcome the problem of damage to a storage tank due to corrosion, but none, alone or in combination, provide a means to know the condition of an anode rod quickly and accurately without costly and dangerous disassembly of a portion of the storage tank.

For example, U.S. Pat. No. 5,373,788 to Guentzler discloses a galvanic anode device having a monitor for indicating the need to replace the anode in an internal combustion engine cooling system. In an embodiment, Guentzler discloses a visual indicator at the outside end of a single vertical through-hole aperture in the anode mounting plug. The anode itself is solid. When the anode is totally depleted at the location of the aperture, this will cause a small leak to occur to indicate that replacement is necessary.

However, the structure disclosed in Guentzler only visually indicates that replacement is necessary after the anode is totally depleted, so there would be no indication of a problem until the fluid leaks from the cooling system through the aperture. In the interim, the cooling system has been exposed to corrosive elements because the anode rod has deteriorated over a period of time during which it did not provide adequate protection to the system. The device disclosed by Guentzler also will leak after the anode breaks. In addition, another shortcoming of the device disclosed by Guentzler is that it functions as an "all or nothing" type system, where the consumer could check the cooling system even minutes before the anode completely breaks away and would be unaware of an impending fluid leak, causing extensive damage to the combustion engine cooling system and the to the surrounding environment.

Another example is U.S. Pat. No. 3,037,920, by Vixler, which discloses an indicator system for sacrificial anodes comprising an ammeter electrically connected between the tank and the anode. The ammeter is indicative of the galvanic current induced in a circuit from the anode, through the water to the interior surface of the tank, and through the low resistance connection of the anode to the tank. Galvanic current within a range could indicate a degree of protection, whereas, levels higher than the range could lead to an early end of life for the anode, and levels lower than the range could signal less than adequate protection for the storage tank. Vixler provides the ammeter with a blocking means as a "trap". When the ammeter is dismounted, the ammeter level is held so that the manufacturer can void the warranty, based on customer neglect for failing to report the status of the excessively low levels.

In addition, U.S. Pat. No. 4,271,120, by Michaud, discloses a device for detecting and indicating the presence of a corrosive fluid in a volume substantially at atmospheric pressure. The device comprises a hollow housing having open inner and outer ends, a primary indicator movably mounted in the housing between a stored position inside the housing and an indicating position outside of the housing, a compression spring in the housing adjacent to and coupled with the primary indicator. A corrodible link holds the spring in compression and the primary indicator in the stored position. When the link is severed, the spring projects the primary indicator from the housing to the indicating position. At least one drawback of this system is that the corrodible link is not the anode, but essentially, a type of mechanical "fuse" that warns of corrosive fluid, which does not necessarily require anode replacement.

Finally, U.S. Pat. No. 3,621,810, by Zuck Jr., also discloses a device for detecting corrosive condition in a fluid containing system.

None of these devices in the prior art, alone or in combination, solves the long-felt need of providing a cost-effective rapid and accurate solution to indicate anode rod depletion to protect the integrity of the tank.

SUMMARY OF THE INVENTION

It is therefore an object of the invention to provide an Anode Rod Depletion Indicator comprising:
  a core wire arranged within an anode rod;
  the core wire having at least one longitudinal passageway and at least one substantially lateral passageway communicating with said longitudinal passageway;
  actuator means in communication with an upper end of the longitudinal passageway;
  indicator means for indicating that the anode rod is depleted, the indicator means being connected to the actuator means;
  wherein when the anode rod is depleted to an extent sufficient to expose a predetermined amount of the core wire so that a fluid surrounding the anode rod flows into the lateral passageway and the longitudinal passageway and pressurizes until reaching a threshold which triggers the actuator; and
  the indicator means is displaced by the actuator means to a position which indicates that the anode rod is depleted.

In an aspect of an embodiment of the invention, the actuator comprises a switch.

In another aspect of an embodiment of the invention, the actuator comprises a pressure gauge.

In another embodiment, the actuator comprises a piston.

The indicator means may include a light which illuminates to indicate that said anode rod is depleted.

The indicator means may include an audible indicator.

The indicator means may also include means for remote indication that the anode rod is depleted.

In an embodiment, the threshold pressure of the fluid which triggers the actuator is reached when the predetermined amount of the hollow core wire which is exposed is at least 6 inches long.

The device may further comprise a switch, and the actuator actuates the switch to cut off at least one of a water feed supply and a fuel supply valve.

In yet another embodiment, an Anode Rod Depletion Indicator comprises:
  a core wire arranged within an anode rod;
  the core wire having at least one fluted portion of a predetermined longitudinal length;
  an actuator in communication with at least the fluted core portion; and
  indicator means for indicating that the anode rod is depleted, said indicator means being connected to the actuator;
  wherein when the anode rod is depleted to an extent sufficient to expose a predetermined amount of the fluted core portion of said core wire so that a fluid which surrounds the anode rod flows into the fluted portion and pressurizes until reaching a threshold which triggers the actuator,
  the indicator means is displaced by said actuator to a position to indicate that the anode rod is depleted.

In yet another embodiment, an Anode Rod Depletion Indicator comprises:
  an anode rod having at least one longitudinal hollowed passageway and at least one substantially lateral hollowed passageway communicating with said longitudinal hollowed passageway;
  actuator means in communication with an upper end of said longitudinal hollowed passageway;
  indicator means for indicating that said anode rod is depleted, said indicator means being connected to said actuator means;
  wherein when said anode rod is depleted to an extent sufficient so that a fluid surrounding said anode rod flows into said lateral hollowed passageway and in said longitudinal hollowed passageway and pressurizes until reaching a threshold which triggers said actuator means; and
  said indicator means is displaced by said actuator means to a position which indicates that said anode rod is depleted.

DETAILED DESCRIPTION OF THE PREFERRED EMBODIMENTS

Figure 1:
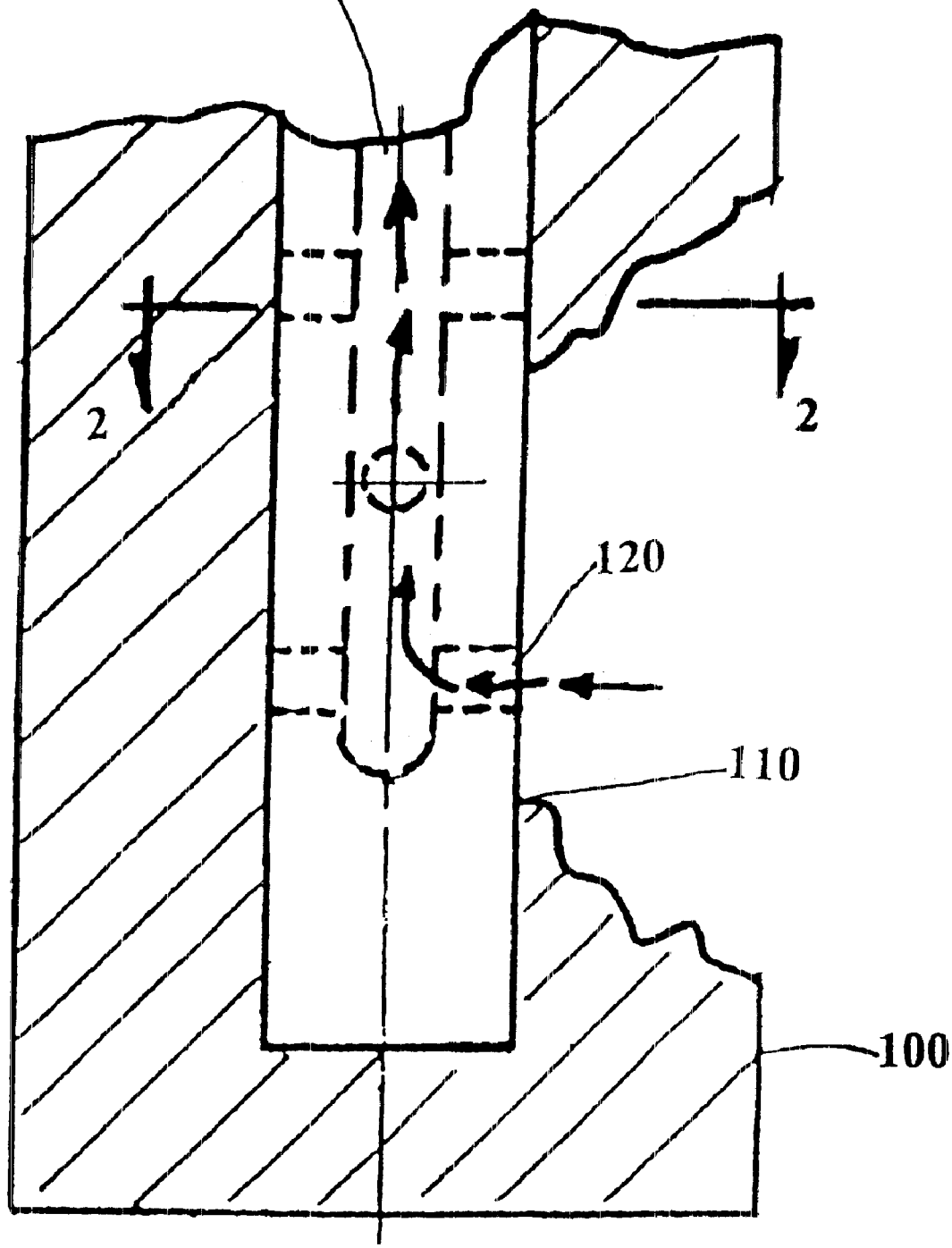
FIG. 1 illustrates a first embodiment according to the present invention.

FIG. 1 illustrates first embodiment of the present invention.

According to FIG. 1, an anode rod 100 contains a hollow core wire 110 arranged therein. In this particular embodiment, the replacement of the anode is based on the replacement of the anode when the exposure of core wire is 6 inches long from either end of the anode, because several manufacturers of anodes recommend replacement when 6 inches of the core wire becomes exposed at either end of the anode. However, the length of the exposure of the hollow core wire necessary to indicate that the anode rod must be replaced may be any predetermined length according to an individual manufacturer's specification and designs, and the hollow core wire of the present invention may also be of any diameter according to need.

Figure 2:
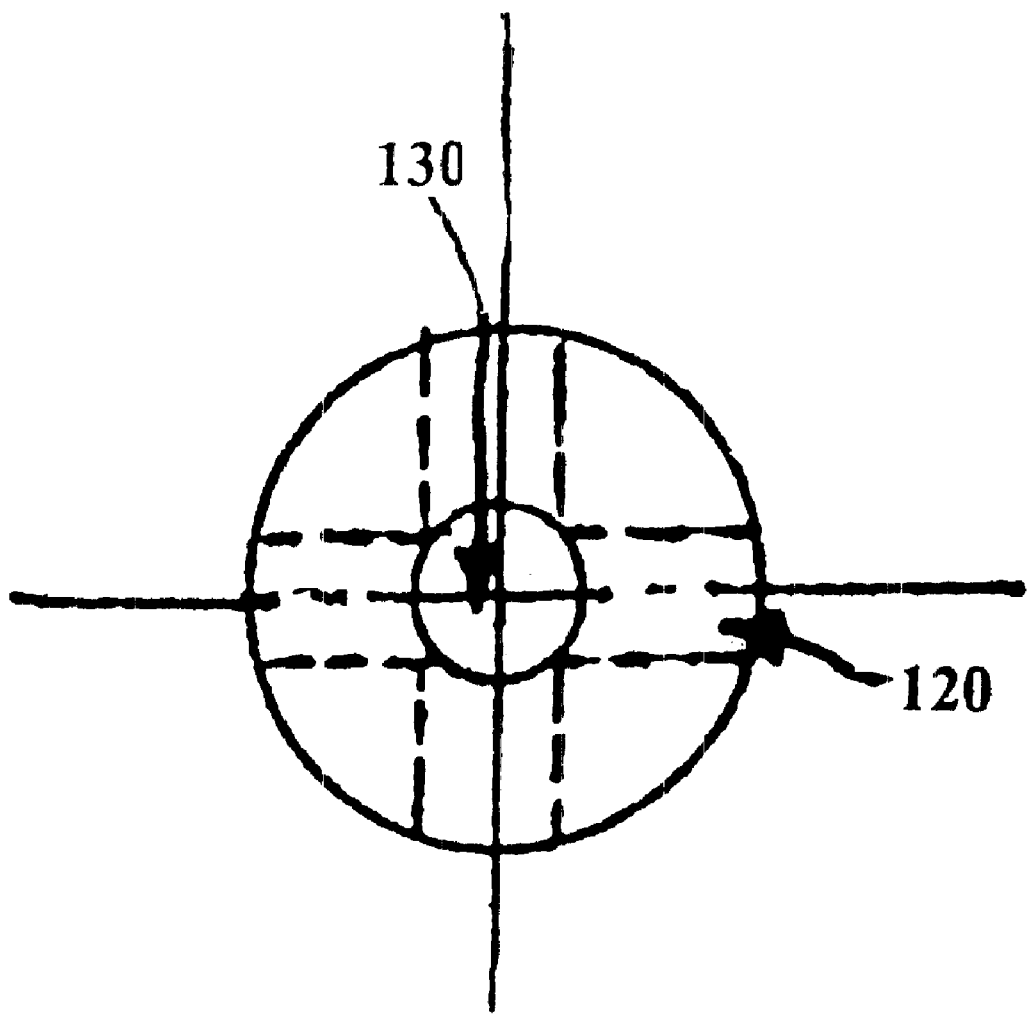
FIG. 2 illustrates a cross section of the anode rod shown in FIG. 1 along the 2—2 line.

FIGS. 1 and 2 illustrate a first embodiment of the present invention shown. In this embodiment, the anode 100 has a hollow core wire 110 that has a longitudinal passageway or center hole 130 and substantially lateral passageways or feed holes 120, so that when the anode has been eaten away to expose a sufficient portion of the core wire 110, the fluid will enter from the lateral feed holes to the center hole and proceed upward until such time and with such pressure as to push the piston (shown in FIGS. 4 and 5) upward. The lateral feed holes may be placed, for example, 6 inches from the top and/or bottom of the anode, or at intervals throughout the length of the anode. Moreover, the 6 inch example is merely for illustrative purposes and the distances may be significantly more or less, according to need.

Finally, it is also within the spirit and scope of the invention that the substantially lateral feed holes may be slanted (not shown) so as to communicate with the center hole at acute or obtuse angles. Even the center hole may in fact be off-centered, according to need.

Figure 3:
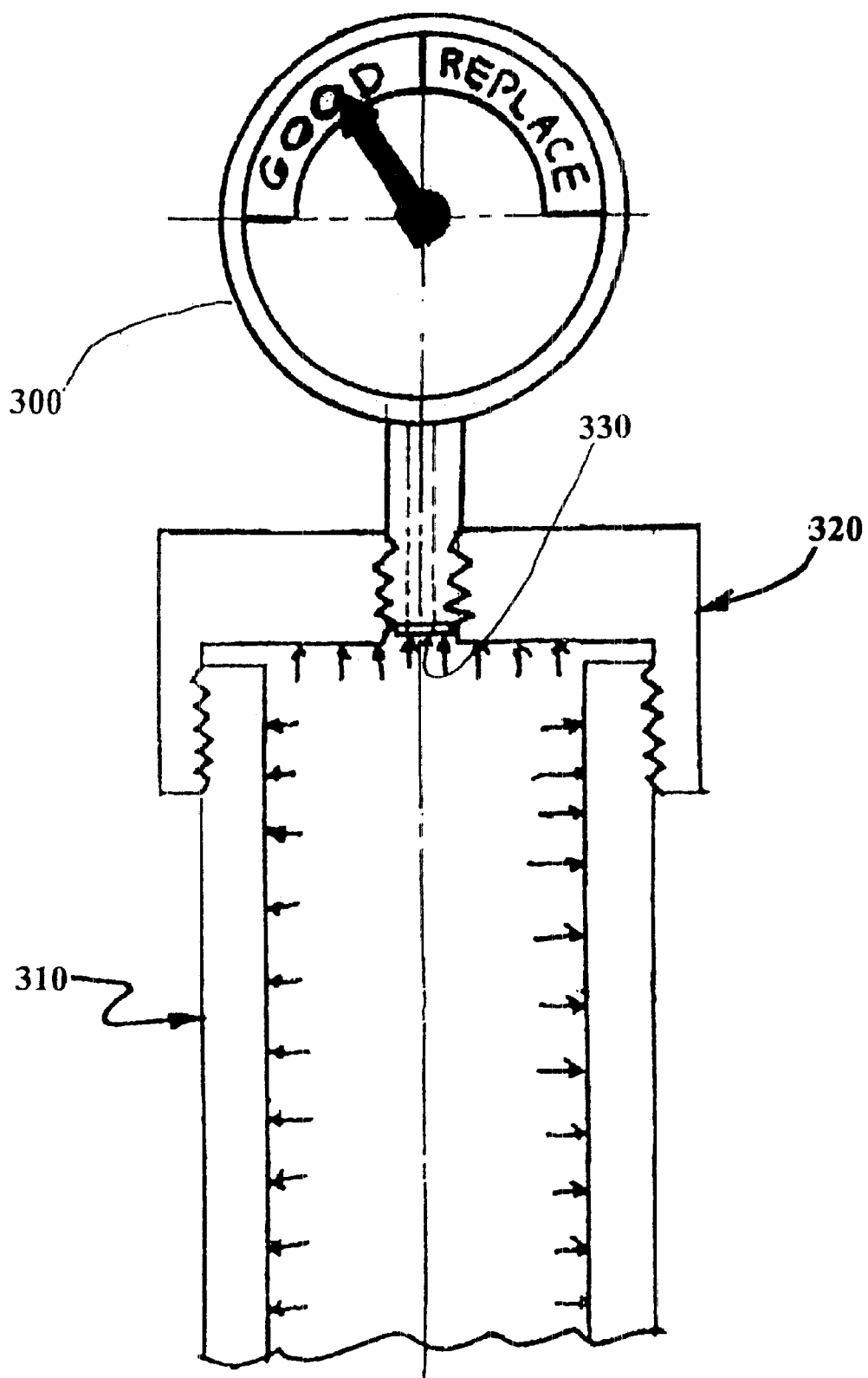
FIG. 3 illustrates a pressure gauge or switch used to indicate the status of anode rod of the present invention.

FIG. 3 shows a pressure gauge or switch 300 which can be activated to alert the consumer to the changed status of the anode rod. The fluid pressure pushes against the anode rod 310 and cap 320. In the center of the cap, there is a contact portion 330, which will actuate the gauge to indicate "replace" once a predetermined threshold pressure is reached. The contact portion may be a transducer that changes states once a certain pressure is reached, or by the fluid pressure on the gauge or by activating a switch. It is even within the spirit and scope of the invention to utilize an optical sensing means, for example, where a path of a beam of light is interrupted by the fluid pressure which pushes the upper portion of a contact into the optic path.

In this embodiment, the lateral holes may be placed within 6 inches from either end of the anode because there is a greater likelihood of the anode being eaten away near the top or bottom than toward the middle. However, a series of lateral holes may be placed at different positions or intervals along the anode.

Moreover, it is within the spirit and scope of the present invention that the diameter and number of the lateral holes, and the diameter of the hollow core wire may be of various sizes and arranged at various positions in the anode. As previously disclosed, the vertical center hole may be off-center, and the lateral holes do not have to be on both sides of the core wire, nor do they have to be in alignment on both sides of the hole.

In addition, the pressure gauge or switch 300 may activate a cutoff switch (not shown) that shuts down the fluid supply (not shown) and/or a fuel supply. The switch could also activate an audible alarm, and/or a remote monitoring site of a service provider. The service provider could either ship a replacement anode to the consumer or indicate that a service person bring a replacement anode during a service visit.

Figure 4:
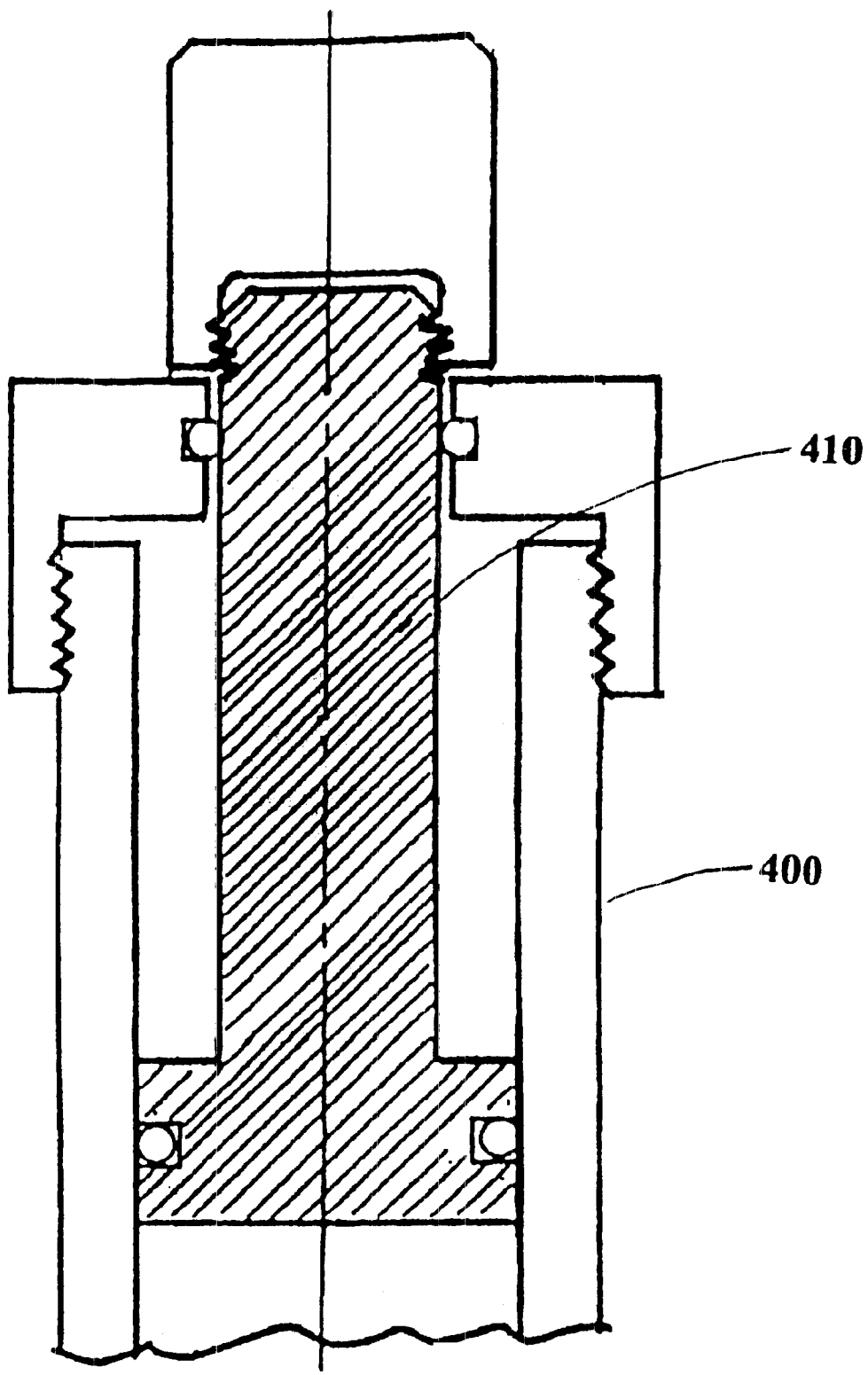
FIG. 4 illustrates a piston used to activate an indicator.
Figure 5:
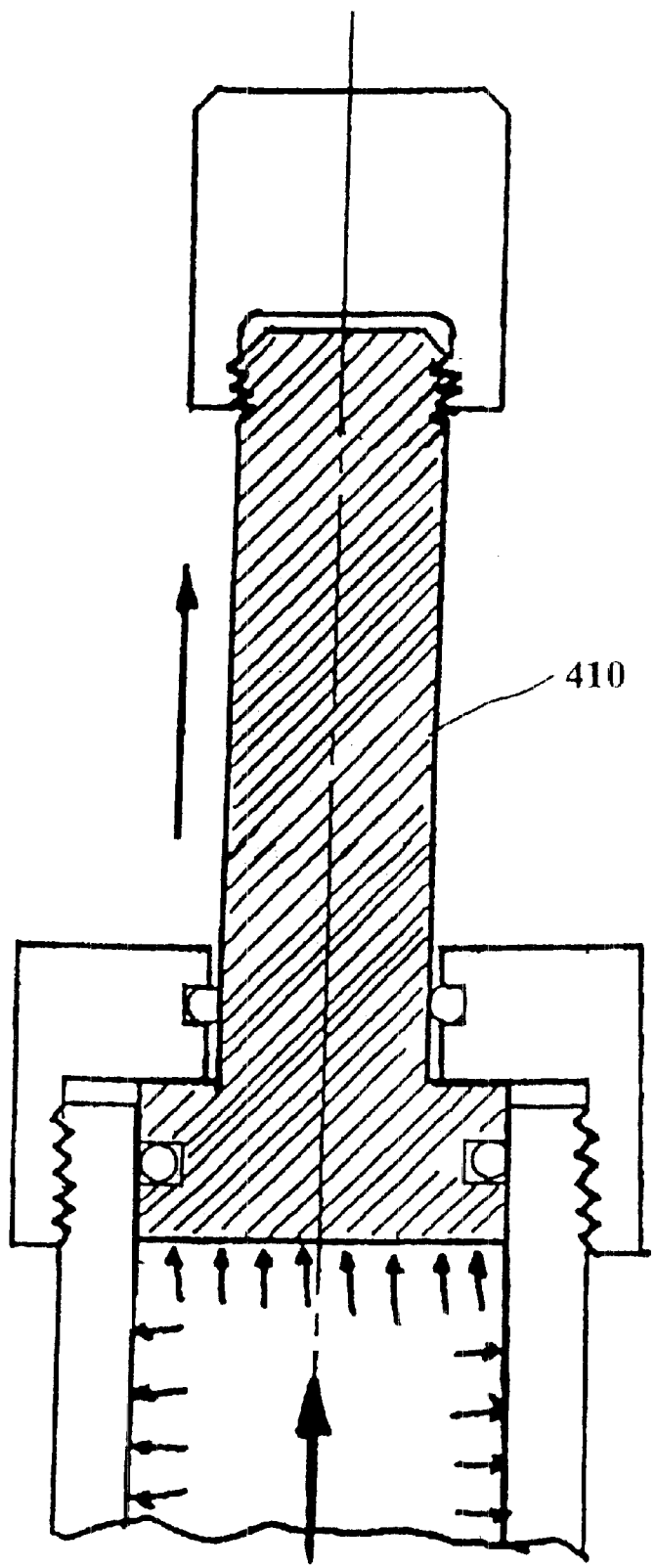
FIG. 5 illustrates the piston of FIG. 4 in an extended position due to fluid pressure.

FIGS. 4 and 5 illustrate a piston assembly 400 in two respective states. FIG. 4 typically would indicate a "good" or normal status.

When the fluid pressure in the hollow core shown in FIG. 1 reaches a threshold level, the piston 410 will be pushed upward to a second state (shown in FIG. 5), which would indicate a "Replace" or "Service" status.

Similar to the first embodiment, the piston assembly 400 may activate a cutoff switch (not shown) that shuts down the fluid supply (not shown) and/or a fuel supply. The switch could also activate an audible alarm, and/or a remote monitoring site of a service provider, which would function as previously described.

Figure 6:
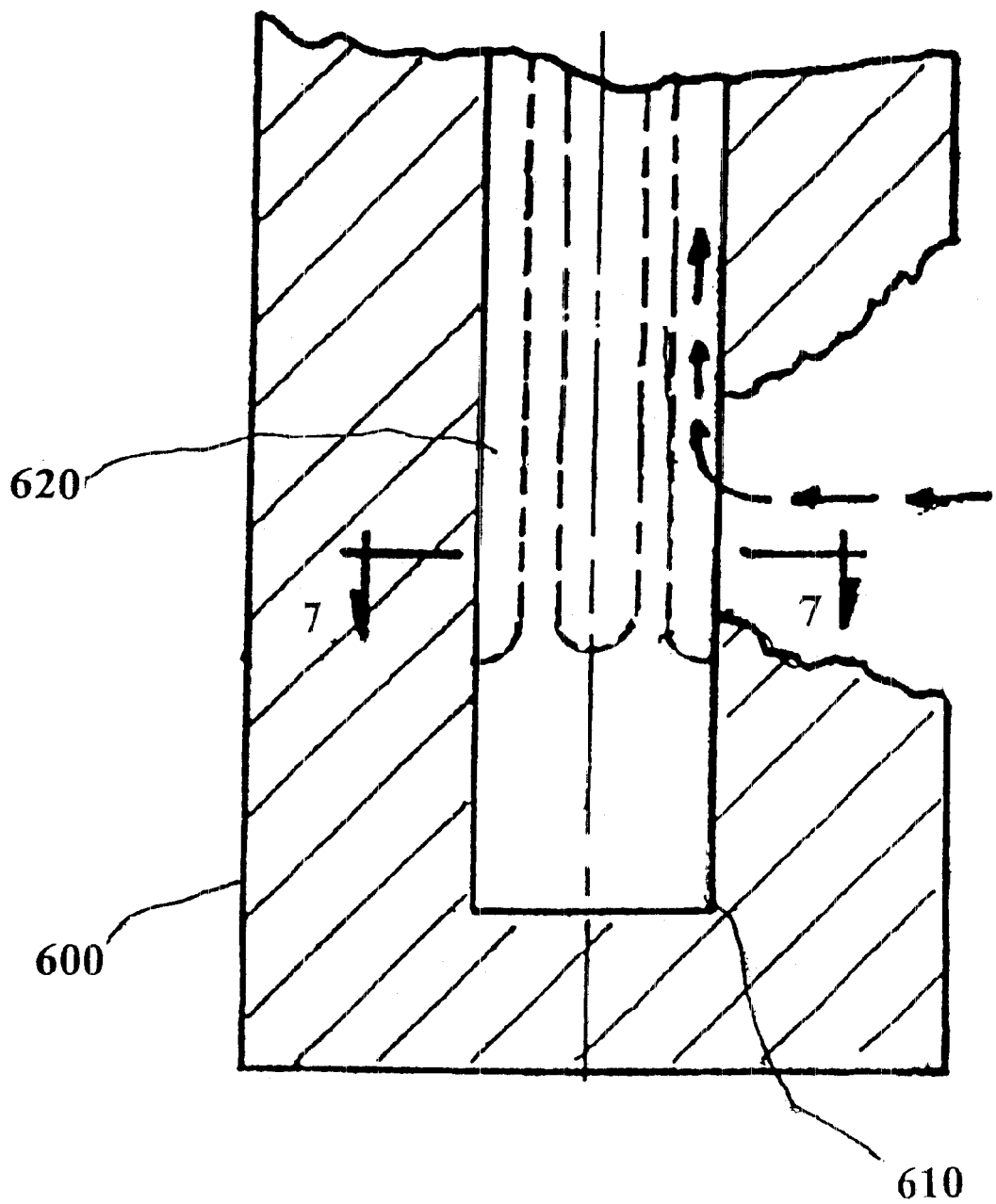
FIG. 6 illustrates a second embodiment of the present invention.
Figure 7:
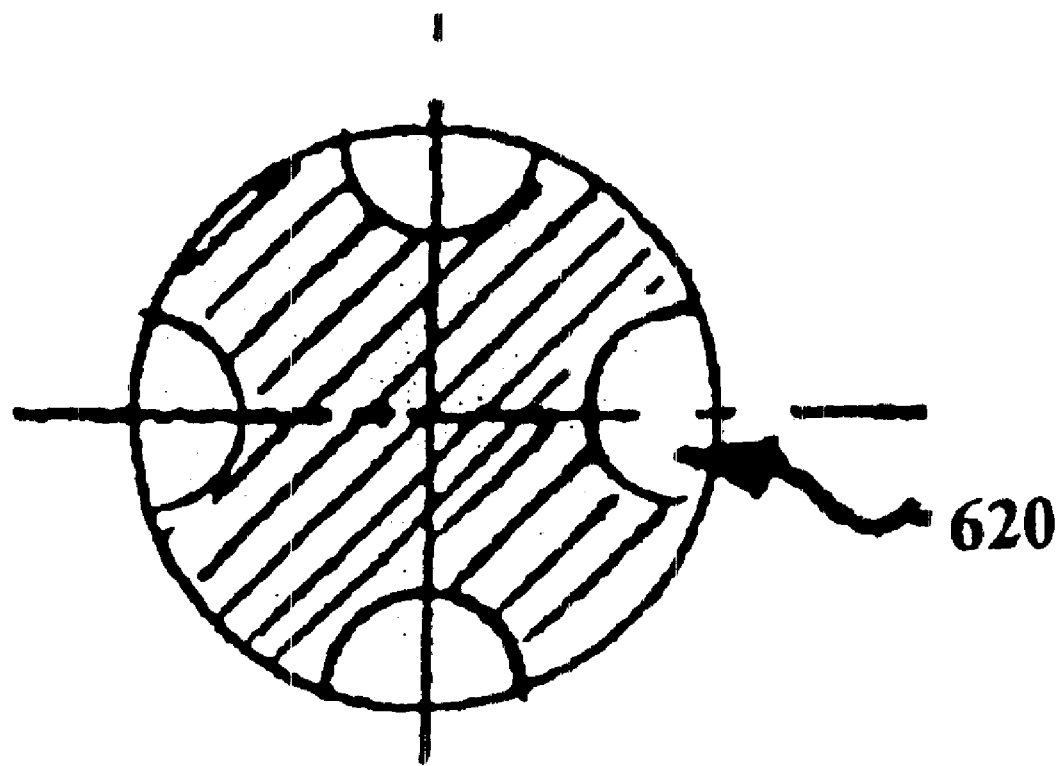
FIG. 7 illustrates a cross section of the anode rod shown in FIG. 1 along the 7—7 line.

As shown in a second embodiment in FIG. 6, the core wire 610 is fluted, as shown by the passageways 620 shown in the cross-sectional view of the core. These fluted passageways 620 permit fluid to flow through when corrosion has eaten away a sufficient portion of the anode 600 to expose the core wire.

As shown by the arrows in FIG. 6, fluid in the tank flows up the flutes 620 once the core wire is exposed.

It is also contemplated that the invention may comprise an anode having the longitudinal and lateral passageways, either without a core wire, or adapted for connection with an electrical source.

The fluid then pressurizes and activates a pressure gauge or switch, or the pressurized fluid can push a piston up into a location where it is visible to the homeowner. The homeowner is alerted to the need for replacing the anode rod to prevent corrosion to the internal tank.

It will be both appreciated and understood by a person of ordinary skill in the art that the amount of pressure which activates the switch can be chosen according to a specific need, dependent upon the size of the tank, the amount of the core wire exposed which activates the "replace" status, the diameter of the core wire, the diameter of holes or the fluted passages, or the angles of the holes, the type of fluid in the tank, the material used in the anode, etc.

It is also to be understood that the invention is not limited to the illustrations described and shown herein, which are deemed to be more illustrative of the best modes of carrying out the invention, and which are susceptible of modification of form, size, arrangement of parts and details of the operation. These modifications are within the spirit and scope of the appended claims.

We claim:

1. A water heater having an anode rod suspended vertically therewithin, said anode rod being an Anode Rod Depletion Indicator consisting essentially of:
    a core wire arranged within an anode rod;
    said core wire having at least one longitudinal passageway and at least one substantially lateral passageway communicating with said longitudinal passageway;
    actuator means in communication with an upper end of said longitudinal passageway;
    indicator means for indicating that said anode rod is depleted, said indicator means being connected to said actuator means;
    wherein when said anode rod is depleted to an extent sufficient to expose a predetermined amount of said core wire so that a fluid surrounding said anode rod flows into said lateral passageway and said longitudinal passageway and pressurizes until reaching a threshold which triggers said actuator;

said indicator means is displaced by said actuator means to a position which indicates that said anode rod is depleted; and wherein said threshold pressure which triggers said actuator is reached when the predetermined amount of exposure of the core wire is at least 6 inches at either end.

2. The device according to claim 1, wherein said actuator means comprises a pressure gauge.

3. The device according to claim 1, wherein said actuator means comprises a piston.

4. The device according to claim 1, wherein said actuator means comprises a switch.

5. The device according to claim 1, wherein said indicator means includes a light for indicating that said anode rod is depleted.

6. The device according to claim 1, wherein said indicator means includes an audible indication.

7. The device according to claim 1, wherein said indicator means includes means for remote indication that said anode rod is depleted.

8. The device according to claim 1, comprising at least a second substantially lateral passageway communicating with said longitudinal passageway.

9. The device according to claim 1, wherein said longitudinal passageway is positioned in the center of said core wire.

10. The device according to claim 1, wherein said longitudinal passageway is offset from a center of said core wire.

11. The device according to claim 1, further comprising a switch; and wherein said actuator means actuates said switch to cut off at least one of a fluid supply and a fuel supply.

12. The device according to claim 1, wherein said substantially lateral passageway is arranged at one of an acute and obtuse angle relative to said longitudinal passageway.

13. An Anode Rod Depletion Indicator for vertical suspended installation in a corrosive fluid tank, said indicator consisting essentially of:

a core wire arranged within an anode rod;

said core wire having at least one fluted portion of a predetermined longitudinal length;

an actuator in communication with at least the fluted core portion; and indicator means for indicating that said anode rode is depleted, said indicator means being connected to said actuator;

wherein when said anode rod is depleted to an extent sufficient to expose a predetermined amount of the fluted core portion of said core wire so that a fluid which surrounds said anode rod flows in the fluted portion and pressurizes until reaching a threshold which triggers said actuator, and said indicator means is displaced by said actuator to a position to indicate that said anode rod is depleted.

14. The device according to claim 13, wherein said actuator comprises a piston.

15. The device according to claim 13, wherein said actuator comprises a pressure gauge.

16. The device according to claim 13, wherein said actuator comprises a switch.

17. The device according to claim 13, wherein, said indicator means includes at least one of an indicator light and an audible indicator to indicate that said anode rod is depleted.

18. The device according to claim 13, wherein said indicator means includes means for remote indication that said anode rod is depleted.

19. The device according to claim 13, wherein the threshold pressure of the fluid to trigger said actuator is reached when the predetermined amount of exposure of the core wire is at least six inches.

20. The device according to claim 13, wherein said indicator means further comprises a switch, and said actuator actuates said switch to cut off at least one of a fluid supply and a fuel supply.

* * * * *